United States Patent
Lange et al.

(10) Patent No.: US 10,023,549 B2
(45) Date of Patent: Jul. 17, 2018

(54) PROCESS FOR THE PRODUCTION OF 1,4-BUTANEDIOL AND TETRAHYDROFURAN FROM FURAN

(71) Applicant: SHELL OIL COMPANY, Houston, TX (US)

(72) Inventors: Jean Paul Andre Marie Joseph Gishlain Lange, Amsterdam (NL); Sipke Hidde Wadman, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/533,014

(22) PCT Filed: Dec. 2, 2015

(86) PCT No.: PCT/EP2015/078347
§ 371 (c)(1),
(2) Date: Jun. 3, 2017

(87) PCT Pub. No.: WO2016/087508
PCT Pub. Date: Jun. 9, 2016

(65) Prior Publication Data
US 2017/0320842 A1    Nov. 9, 2017

(30) Foreign Application Priority Data
Dec. 4, 2014 (EP) ................................ 14196391

(51) Int. Cl.
*C07C 29/17* (2006.01)
*C07C 41/20* (2006.01)
*C07D 307/08* (2006.01)
*B01J 23/656* (2006.01)

(52) U.S. Cl.
CPC ........ *C07D 307/08* (2013.01); *B01J 23/6567* (2013.01); *C07C 29/172* (2013.01); *C07C 41/20* (2013.01)

(58) Field of Classification Search
CPC ............................. C07C 29/172; C07C 41/20
See application file for complete search history.

(56) References Cited

U.S. PATENT DOCUMENTS

| 4,550,185 | A | * | 10/1985 | Mabry | ................. | B01J 23/6567 502/325 |
| 5,905,159 | A | * | 5/1999 | Fischer | ................. | C07C 29/132 549/429 |
| 5,945,571 | A | * | 8/1999 | Pinkos | ................. | C07C 29/132 568/865 |
| 2006/0004212 | A1 | | 1/2006 | Bhattacharyya et al. | | |

OTHER PUBLICATIONS

Hu, X. et al. "Upgrading biomass-derived furans via acid-catalysis/hydrogenation: the remarkable difference between water and methanol as the solvent" Green Chem., 2015, 17, 219-224; Published Oct. 7, 2014 (Year: 2014).*

* cited by examiner

*Primary Examiner* — Medhanit W Bahta

(57) ABSTRACT

The present invention provides a process for the preparation of 1,4-butanediol and tetrahydrofuran said process comprising contacting furan with hydrogen and water in the presence of a supported catalytic composition comprising rhenium and palladium in a weight ratio of at least 1:1 and a total combined weight rhenium and palladium in the catalyst composition in the range of from 0.01 to 20 wt %.

7 Claims, No Drawings

PROCESS FOR THE PRODUCTION OF 1,4-BUTANEDIOL AND TETRAHYDROFURAN FROM FURAN

PRIORITY CLAIM

The present application is the National Stage (§371) of International Application No. PCT/EP2015/078347, filed Dec. 2, 2015, which claims priority from European Patent Application No. 14196391.8, filed Dec. 4, 2014 incorporated herein by reference.

FIELD OF THE INVENTION

The present invention relates to a process for the production of 1,4-butanediol and tetrahydrofuran from furan.

BACKGROUND OF THE INVENTION

Furan and its derivatives are useful precursors for industrial chemicals in the area of, for example, pharmaceuticals, herbicides and polymers. Furan may be converted into tetrahydrofuran (THF) and 1,4-butanediol (1,4-BDO). THF and 1,4-BDO are valuable chemicals used industrially as solvents and in the production of elastic fibres such as elastane/spandex, polybutyrate terephthalate and derivatives of gamma butyrolactone.

These chemicals are usually produced industrially via a number of routes from petrochemical feedstocks, obtainable from fossil fuels. One industrial route for the production of 1,4-BDO requires the reaction of acetylene with two equivalents of formaldehyde followed by hydrogenation of the resultant 1,4-butynediol to form 1,4-butanediol. In an alternative process, propylene oxide is converted to allyl alcohol. The allyl alcohol is then hydroformylated to form 4-hydroxybutyraldehyde, which may be hydrogenated to form 1,4-butanediol. Other traditional routes use butadiene, allyl acetate or succinic acid as starting materials.

1,4-butanediol may also be produced as a side-product in a method for making tetrahydrofuran (THF) by oxidizing n-butane to crude maleic anhydride followed by catalytic hydrogenation.

In recent years, increased efforts have focused on producing chemicals, including 1,4-BDO and THF, from renewable feedstocks, such as sugar-based materials.

A method for obtaining furan from non-fossil fuel based sources involves the decarbonylation of furfural. Examples of reaction processes for achieving this and the subsequent conversion of the furan into its derivatives can be found in Hoydonck, H E; Van Rhijn, W M; Van Rhijn, W; De Vos, D E; & Jacobs, P A; (2012) Furfural and Derivatives, in Ullmann's Encyclopedia of Industrial Chemistry (volume 16, pp 285-313), Wiley-VCH Verlag GmBH & Co. KGaA, Weinheim; Dunlop, A P; and Peters, F N; in The Furans Reinhold Publ. Co, 1953; K. J. Zeitsch, in "The Chemistry and Technology of Furfural and its Many By-products" Sugar Series 13, Elsevier, 2000; Lange, J-P; van der Heide, E; van Buijtenen, J; and Price, R; Furfural—A Promising Platform for Lignocellulosic Biofuels; ChemSusChem 2012, 5, 150-166 and Watson, J. M.; Ind. Eng. Chem. Prod. Res. Develop., 1973, 12(4), 310. Furfural may be obtained from hemicellulose via acid hydrolysis in the liquid phase as well as in the gas phase as described in WO 2002/22593 and WO 2012/041990.

The conversion of furan to THF and 1,4-BDO by hydrogenation in the presence of water, acetic acid and Raney nickel or oxide supported nickel catalyst is described in Watson, J M; Ind. Eng. Chem. Prod. Res. Develop., 1973, 12(4), 310.

A process for the conversion of furan into 1,4-BDO and THF is taught in U.S. Pat. No. 5,905,159. This document teaches a process in which furan is converted as a reaction mixture with water and in the presence of hydrogen but in the absence of a water-soluble acid in a single stage over a hydrogenation catalyst. The hydrogenation catalyst of U.S. Pat. No. 5,905,159 contains at least one element of subgroup I, V, VI, VII or VIII in the form of a compound or in elemental form, with the restriction that the catalyst does not contain nickel alone being applicable. The preferred catalyst in this process is Re/Ru on active carbon. A similar catalyst is used in the process described in Pan, T; Deng, J; Xu, Q; Zuo, Y; Guo, Q-X and Fu, Y; Catalytic Conversion of Furfural into a 2,5-Furandicarboxylic Acid-based Polyester with Total Carbon Utilisation; ChemSusChem 2013, 6, 47-50.

Known methods in the art provide a mixture of THF, 1,4-BDO and n-butanol. As indicated above, THF and 1,4-BDO are valuable chemicals. However, n-butanol is currently of lower commercial value.

It would be advantageous to provide a method for the production of 1,4-butanediol and tetrahydrofuran from furan in which the amount of n-butanol, relative to that of 1,4-BDO and THF, produced is reduced and/or which can be tailored to produce a specific product range.

SUMMARY OF THE INVENTION

Accordingly, the present invention provides a process for the preparation of 1,4-butanediol and tetrahydrofuran said process comprising contacting furan with hydrogen and water in the presence of a supported catalytic composition comprising rhenium and palladium in a weight ratio of at least 1:1 and a total combined weight rhenium and palladium in the catalyst composition in the range of from 0.01 to 20 wt %.

DETAILED DESCRIPTION OF THE INVENTION

The present inventors have found that a catalyst comprising rhenium and palladium on a support is highly effective in the conversion of furan to 1,4-butanediol and tetrahydrofuran without the production of large amounts of n-butanol as a side product.

The rhenium and palladium may be present on the catalyst in their elemental form or as compounds.

The method of application of the rhenium and palladium to the support is not critical and may be effected in a wide range of ways. The rhenium and palladium may be applied to the support using the same or different methods and either sequentially of simultaneously. Preferably, it is more efficient to apply the two metals using the same method. Suitable methods include, for example, impregnation of the support with solutions or suspensions of the salts, complexes, hydroxides, oxides or other organic or inorganic compounds of the relevant elements, drying and optional calcination. Another possibility for applying the rhenium and palladium to the support is to impregnate the latter with a solution of thermally readily decomposable complexes, for example with carbonyl or hydride complexes of the rhenium and/or palladium, and to heat the carrier thus impregnated to, for example, 150 to 600° C. for thermal decomposition of the absorbed metal compounds. The rhenium and/or palladium may furthermore be deposited on the catalyst carrier by vapour deposition or by flame spraying. Subsequent reduction of the metal compound to the relevant metals or compounds of lower oxidation states by means of a reducing agent may be carried out after any method of deposition.

The rhenium and palladium are present on the finished catalyst in a weight ratio of at least 1:1. This ratio is the weight ratio of the metals considered as elements in the catalyst with which the furan is brought into contact. More preferably, the weight ratio of rhenium:palladium is at least 5:1, more preferably at least 10:1, even more preferably at least 20:1. Further advantages, such as increased yields of BDO may be obtained by even higher weight ratios, for example at least 50:1.

The total amount of the metals (considered as their elements) on the catalyst may vary within wide ranges, and may be of from 0.01 to 20 wt %, 0.1 to 10 wt % or 0.5 to 5 wt % on the basis of the total weight of the catalyst. Preferably, the total amount of said metal or metals is at least 0.01 wt %, more preferably at least 0.03 wt %, more preferably at least 0.1 wt %, more preferably at least 0.3 wt %, more preferably at least 1.0 wt %, most preferably at least 3.0 wt %. Further, preferably, the total amount of said metal or metals is at most 20 wt %, more preferably at most 15 wt %, most preferably at most 10 wt.

Suitable supports in the present invention include oxides of aluminium, titanium, zirconium, silicon, as such or in combination with other oxides. The support can be amorphous or crystalline, including clays such as montmorillonite or zeolites, such as ZSM-5 or ZSM-10 zeolites. In another embodiment, the support is composed of carbon such as active carbon. Mixtures of different supports can, of course, also serve as supports for the catalysts to be used in the process of the invention. Preferred supports are aluminas, titanium oxides, zirconium dioxide and active carbon. More preferred are zirconium dioxide and active carbon. Most preferably, the support is active carbon.

The furan may be contacted with hydrogen either in the gas or the liquid phase.

Suitable conditions for the production of 1,4-BDO and THF from furan include gas- or liquid phase conditions in the absence or presence of gas or liquid diluent. For liquid phase condition, an inert non-polar or moderately polar solvent, such as a hydrocarbon or oxygenate, can be used. Further conditions include a temperature in the range of from 25 to 250° C., a pressure of from 0.1 to 15 MPa and a $H_2$:furan molar ratio in the range of from 0.2:1 to 100:1, preferably in the range of from 0.2:1 to 10:1 and most preferably in the range from 1:1 to 3:1.

Alternative suitable conditions for the production of a mixture of BDO and THF include co-feeding water as a gas or liquid at a water:furan molar ratio in the range of from 0.2:1 to 100:1, preferably in the range of 1:1 to 20:1 and most preferably 3:1 to 10:1. In this embodiment, further suitable conditions include the use of a solvent comprising water and/or oxygenates, preferably the reaction product (THF) or eventually by-products, a temperature in the range of from 100 to 350° C., preferably 120 to 250° C., most preferably 150-200° C., a pressure of from 0.1 to 15 MPa, preferably 1-10 MPa and most preferably 3-7 MPa and a $H_2$:furan molar ratio in the range of from 0.2:1 to 100:1, preferably in the range of from 1:1 to 10:1, most preferably 2:1 to 5:1.

The invention will now be illustrated by the following non-limiting examples.

EXAMPLES 1 to 20

A number of catalysts were evaluated in a 16-reactor testing unit that can operate at up to 80 bar and 500° C. The testing unit can be fed with up to 5 gases (hydrogen, CO, $N_2$, argon and air) and two liquids. The unit allowed for on-line GC analysis of gases and semi-automated off-line GC analysis of the liquid product. Gas and liquid product yields were determined in reference to a gas standard (He) and a liquid standard (diethylene-glycol diethyl ether) that were fed together with the gas and liquid feed and were selectively collected in the gas and liquid samples, respectively.

The reactor consisted of SS316 tubes of 4.6 mm ID and 35.5 cm long, of which the central 10 cm length is isothermal. The reactor tubes were loaded with about 1 mL of catalyst, centered in the middle of the reactor while the remaining upper and lower void was filled with inert material such as SiC particles and/or porous SS316 cyclinders.

The catalysts were prepared by incipient wetness impregnation of the support with solutions of the following salts: $Pd(NH_3)_4(NO_3)_2$, $Pt(NH_3)_4(NO_3)_2$, $HReO_4$, $Co(NO_3)_2.6H_2O$, $Ru(NO_3)_3NO$. The solutions were prepared with the concentration required to achieve the targeted metal loading. The catalysts were dried at 120° c. for 2 h in air and for half an hour at 225° C. temperature.

The catalysts supports consisted 30-80 mesh powders of monoclinic zirconia, anatase-rich titania (P25 from Degussa) and active carbon (RX-3 from Norit). Their properties are the following:

TABLE 1

| Support Properties | | |
|---|---|---|
| | BET m2/g | Pore volume ml/g |
| m-ZrO2 | 51.6 | 0.25 |
| TiO2 (P25) | 41.9 | 0.26 |
| C (RX-3) | 1190 | 0.81 |

The catalysts were dried and reduced for 1 h at 75° C., 4 h 120° C. and more than 4 h at 275° C. under a 30% $H_2$/70% $N_2$ flow of GHSV=625 NL/L/h at nearly atmospheric pressure. Subsequently, the temperature was lowered to 120° C., the pressure was raised to 50 atmosphere and the gas flow set to about GHSV=280 Nl/L/h and 100% $H_2$ to be ready for start-up.

The gas feed consisted of a mixture of 10% He and 90% $H_2$ and was fed at a rate of about 280 Nl per liter catalyst bed per hour. The liquid feed consisted of a mixture of 24 w % furan, 21 w % water, 50 w % ethanol and 4 w % standard. The liquid feed was introduced at a rate of about 0.8 litre per litre catalyst bed per hour. The run was carried out at a pressure of 50 bars. The temperature was ramped from 140 to 200° C. by steps of 20° C. and back to 160° C. The run lasted for 200-250 hours in total.

The average yields measured at 160° C. are reported in tables 2 and 3. The yields are expressed as fraction of the carbon of furan that is converted into the desired concerned. The yield may occasionally add up to slightly more than 100 C % as results of experimental inaccuracies.

As shown in these tables, Pd-doped catalysts show a lower co-production of NBA than the corresponding non-Pd catalysts supported on C.

The same is observed for the catalysts supported in $ZrO_2$ or $TiO_2$: The various Pd-doped catalysts show lower NBA co-production than the non-Pd doped catalysts, though these catalysts are more selective for THF and much less for BDO.

In general, the NBA yields are below 5 C % for Pd-based catalysts and >10 C % for Co, Pt, and Ru-based catalysts.

It should be clear to the skilled person that total yields above 100% can be attributed to experimental errors.

TABLE 2

Pd Catalysts Operating at 160° C.

| | support | M1 | Re/M1 g/g | Re w % | M1 w % | THF Yield C % | BDO Yield C % | NBA Yield C % | NBA/BDO C/C |
|---|---|---|---|---|---|---|---|---|---|
| 1 | Carbon | Pd | 103 | 4.0 | 0.039 | 44.7 | 17.6 | 3.7 | 0.2 |
| 2 | Carbon | Pd | 10 | 5.0 | 0.5 | 98.0 | 1.4 | 0.9 | 0.6 |
| 3 | TiO2 | Pd | 6 | 3.0 | 0.5 | 66.7 | 2.0 | 0.7 | 0.4 |
| 4 | TiO2 | Pd | 50 | 5.0 | 0.1 | 70.6 | 1.4 | 1.2 | 0.8 |
| 5 | TiO2 | Pd/Ag/Fe | 1 | 1.6 | 0.077 Pd 1.0Ag 0.1Fe | 96.6 | 0.6 | 0.5 | 0.8 |
| 6 | ZrO2 | Pd | 6 | 3.0 | 0.5 | 38.0 | 9.0 | 0.9 | 0.1 |
| 7 | ZrO2 | Pd | 50 | 5.0 | 0.1 | 73.8 | 0.9 | 3.8 | 4.2 |
| 8 | ZrO2 | Pd | 1 | 0.5 | 0.5 | 108.9 | 0.7 | 0.1 | 0.1 |

TABLE 3

Non-Pd Based Catalysts Operating at 160° C.

| | support | M1 | Re/M1 g/g | Re w % | M1 w % | THF Yield C % | BDO Yield C % | NBA Yield C % | NBA/BDO C/C |
|---|---|---|---|---|---|---|---|---|---|
| 9 | Carbon | Co | 4 | 4.0 | 1.0 | 27.9 | 14.2 | 11.0 | 0.8 |
| 10 | Carbon | Pt | 10 | 5.0 | 0.5 | 63.9 | 12.2 | 12.7 | 1.0 |
| 11 | Carbon | Pt | 73 | 4.0 | 0.055 | 17.0 | 8.2 | 3.6 | 0.4 |
| 12 | TiO2 | Pt | 50 | 5.0 | 0.1 | 48.9 | 4.2 | 20.5 | 4.9 |
| 13 | ZrO2 | Pt | 50 | 5.0 | 0.1 | 48.0 | 1.7 | 18.8 | 10.9 |
| 14 | ZrO2 | Pt | 6 | 3.0 | 0.5 | 49.8 | 0.8 | 17.3 | 22.0 |
| 15 | Carbon | Ru | 5 | 5.0 | 1.0 | 66.0 | 12.1 | 15.6 | 1.3 |
| 16 | Carbon | Ru | 10 | 2.0 | 0.2 | 3.3 | 3.7 | 3.3 | 0.9 |
| 17 | TiO2 | Ru | 100 | 10 | 0.1 | 24.4 | 3.0 | 10.3 | 3.4 |
| 18 | TiO2 | Ru | 10 | 10 | 1.0 | 59.1 | 1.7 | 26.9 | 16.0 |
| 19 | TiO2 | Ru | 10 | 5.0 | 0.5 | 58.1 | 1.3 | 22.8 | 17.3 |
| 20 | TiO2 | Ru | 3 | 5.0 | 2.0 | 48.3 | 0.1 | 10.5 | 70.7 |

When comparing the different metals combined with rhenium on each support, it can clearly be seen that the inventive catalysts provide good overall yields and a desirably low NBA/BDO ratio.

That which is claimed is:

1. A process for the preparation of 1,4-butanediol and tetrahydrofuran said process comprising contacting furan with hydrogen and water in the presence of a supported catalytic composition comprising rhenium and palladium in a weight ratio of rhenium to palladium of at least 1:1 and a total combined weight rhenium and palladium in the catalyst composition in the range of from 0.01 to 20 wt %.

2. A process according to claim 1, wherein the support in the supported catalyst composition is selected from the group consisting of aluminas, titanium oxides, zirconium dioxides, mixtures thereof and carbon.

3. A process according to claim 1, wherein rhenium and palladium are present in the supported catalyst composition in a weight ratio of rhenium to palladium of at least 5:1.

4. A process according to claim 2, wherein rhenium and palladium are preferably present in the supported catalyst composition in a weight ratio of rhenium to palladium of at least 10:1.

5. A process according to claim 1, wherein the total amount of rhenium and palladium on the catalyst is in the range of from 0.1 to 10 wt %.

6. A process according to claim 1, wherein the furan is contacted with hydrogen in the liquid phase at a temperature in the range of from 25 to 250° C., a pressure of from 0.1 to 15 MPa and a $H_2$:furan molar ratio in the range of from 0.2:1 to 100:1.

7. A process according to claim 1, wherein the furan is contacted with hydrogen and water is co-fed at a water:furan molar ratio in the range of from 0.2:1 to 100:1, at a temperature in the range of from 100 to 350° C., a pressure of from 0.1 to 15 MPa and a $H_2$:furan molar ratio in the range of from 0.2:1 to 100:1.

* * * * *